US010739298B2

(12) United States Patent
Yakushenko et al.

(10) Patent No.: US 10,739,298 B2
(45) Date of Patent: Aug. 11, 2020

(54) METHOD FOR PRODUCING A DEVICE FOR ELECTROCHEMICAL DETECTION OF MOLECULES BY WAY OF REDOX CYCLING, DEVICE THEREFOR AND THE USE THEREOF

(71) Applicant: Forschungszentrum Juelich GmbH, Juelich (DE)

(72) Inventors: Alexey Yakushenko, Aachen (DE); Bernhard Wolfrum, Unterschleissheim (DE); Nouran Yehia Adly Hassan, Aachen (DE); Andreas Offenhausser, Aachen (DE)

(73) Assignee: Forschungszentrum Juelich GmbH (DE)

( * ) Notice: Subject to any disclaimer, the term of this patent is extended or adjusted under 35 U.S.C. 154(b) by 274 days.

(21) Appl. No.: 15/567,752

(22) PCT Filed: Apr. 9, 2016

(86) PCT No.: PCT/DE2016/000154
§ 371 (c)(1),
(2) Date: Oct. 19, 2017

(87) PCT Pub. No.: WO2016/180385
PCT Pub. Date: Nov. 17, 2016

(65) Prior Publication Data
US 2018/0088072 A1     Mar. 29, 2018

(30) Foreign Application Priority Data

May 8, 2015   (DE) .................. 10 2015 005 781

(51) Int. Cl.
*G01N 27/327*     (2006.01)
*C09D 11/322*     (2014.01)
(Continued)

(52) U.S. Cl.
CPC ............ *G01N 27/3277* (2013.01); *B41J 2/01* (2013.01); *C09D 11/00* (2013.01); *C09D 11/322* (2013.01);
(Continued)

(58) Field of Classification Search
CPC ........................................ G01N 27/327–3272
See application file for complete search history.

(56) References Cited

U.S. PATENT DOCUMENTS 5,916,156 A * 6/1999 Hildenbrand .......... C12Q 1/002
                                                                                           204/403.11
6,054,039 A * 4/2000 Shieh ..................... G01N 33/66
                                                                                           204/403.06
(Continued)

FOREIGN PATENT DOCUMENTS

CN     1025076888 B     3/2014
EP       0973028 A2     1/2000

OTHER PUBLICATIONS

Strayer et al., "A simple method to fabricate electrochemical sensor systems with predictable high-redox cycling amplification," Lab Chip, 2012, 12, 1548 (Year: 2012).*

(Continued)

*Primary Examiner* — Alexander S Noguerola
(74) *Attorney, Agent, or Firm* — Jordan and Koda, PLLC (57) ABSTRACT

The invention relates to a method for producing a device for the electrochemical detection of molecules by way of redox cycling, to a device therefor, and to the use thereof. A porous dielectric layer is present between two electrode layers, which is able to receive redox-active molecules and may be biofunctionalized. The individual layers are preferably applied by way of an ink jet printing method.

18 Claims, 2 Drawing Sheets

(51) Int. Cl.
| | |
|---|---|
| *C12Q 1/00* | (2006.01) |
| *G01N 33/543* | (2006.01) |
| *C12Q 1/68* | (2018.01) |
| *C09D 11/54* | (2014.01) |
| *H05K 1/00* | (2006.01) |
| *G01N 27/49* | (2006.01) |
| *B41J 2/01* | (2006.01) |
| *C09D 11/00* | (2014.01) |
| *C09D 11/52* | (2014.01) |
| *G01N 33/487* | (2006.01) |

(52) U.S. Cl.
CPC .............. *C09D 11/52* (2013.01); *C09D 11/54* (2013.01); *C12Q 1/001* (2013.01); *C12Q 1/68* (2013.01); *G01N 27/327* (2013.01); *G01N 27/3278* (2013.01); *G01N 27/49* (2013.01); *G01N 33/48721* (2013.01); *G01N 33/5438* (2013.01); *H05K 1/00* (2013.01); *G01N 27/3276* (2013.01); *G01N 2333/77* (2013.01)

(56) References Cited

U.S. PATENT DOCUMENTS

| | | | | |
|---|---|---|---|---|
| 7,086,277 | B2* | 8/2006 | Tess et al. ............... | C12Q 1/004 204/403.1 |
| 7,285,198 | B2* | 10/2007 | Douglas ................. | B82Y 30/00 204/400 |
| 2002/0090649 | A1 | 7/2002 | Chan | |
| 2003/0108922 | A1 | 6/2003 | Fritsch | |
| 2004/0140209 | A1 | 7/2004 | Choi | |
| 2009/0310743 | A1 | 12/2009 | Carpenter et al. | |
| 2012/0181184 | A1 | 7/2012 | Whitesides | |
| 2012/0255860 | A1* | 10/2012 | Briman ................... | H01B 1/04 204/403.15 |

OTHER PUBLICATIONS

Pages 19-23 of the Thesis of Maarten van Megen entitled "Redox cycling at nanospaced electrodes" University of Twente, 2013 (Year: 2013).*

Product description of 3M™ Double Coated Dielectric Tape 3514 (Year: 2014).*

The Pacific Coast Composites product description of CAB-O-SIL M5, downloaded Dec. 11, 2019 from https://www.pccomposites.com/product/cab-o-sil-m5/ (Year: 2019).*

Buckley, AM; Greenblatt, M, Journal of Chemical Education, vol. 71, No. 7, 1994, pp. 599-602.

Goluch E.D.; Wolfrum B.; Singh P.S.; Zevenbergen M.A.G.; Lemay S.G.: "Redox cycling in nanofluidic channels using interdigitated electrodes", Anal Bioanal Chem, vol. 394, 2009, pp. 447-456, XP019702599.

Gross A.J.; Holmes S.; Dale S.E.C.; Smallwood M.J.; Green S.J.; Winlove C.P.; Benjamin N.; Ninyard R.G.; Marken F.: "Nitrite/Nitrate detection in serum based on dual-plate generator-collector currents in a microtrench", Talanta, vol. 131, 2015, pp. 228-235, XP055166031, DOI: doi:10.1016/j.talanta.2014.07.084.

Hüske M.; Stockmann R.; Offenhäusser A.; Wolfrum B: "Redox Cycling in nanoporous electrochemical devices", Nanoscale, vol. 6, 2014, pp. 589-598, XP055291342, DOI: doi:10.1039/C3NR03818A.

Kätelhön E.; Hofmann B.; Lemay S.G.; Zevenbergen M.A.G.; Offenhäusser A.; Wolfrum B.: "Nanocavity Redox Cycling Sensors for the Detection of Dopamine Fluctuations in Microfluidic Gradients", Anal Chem, vol. 82, 2010, pp. 8502-8509, XP055003585, DOI: doi:10.1021/ac101387f.

Martin Hüske et al: "Redox cycling in nanoporous electrochemical devices", Nanoscale, vol. 6, No. 1, Jan. 1, 2014 (Jan. 1, 2014), United Kingdom, pp. 589-598, XP055291342, ISSN: 2040-3364, DOI: 10.1039/C3NR03818A*.

Pandey Manju et al: "Nanoporous alumina ([gamma]- and [alpha]-phase) gel cast thick film for the development of trace moistur", Journal of Sol-Gel Science and Technology, Springer, New York, NY, US, vol. 68, No. 2, Oct. 10, 2013 (Oct. 10, 2013), pp. 317-323, XP035374710, ISSN: 0928-0707, [retrieved on Oct. 10, 2013], DOI: 10.1007/S10971-013-3171-X*.

Wolfrum B.; Zevenbergen M.; Lemay S.: "Nanofluidic redox cycling amplification for the selective detection of catechol", Anal Chem, vol. 80, 2008, pp. 972-977, XP055003581, DOI: doi:10.1021/ac7016647.

Sevenbergen M.A.G; Singh P.S.; Goluch E.D.; Wolfrum B.L.; Lemay S.G: "Stochastic sensing of single molecules in a nanofluidic electrochemical device", Nano Lett., vol. 11, 2011, pp. 2881-2886, XP055166036, DOI: doi:10.1021/nl2013423.

* cited by examiner

METHOD FOR PRODUCING A DEVICE FOR ELECTROCHEMICAL DETECTION OF MOLECULES BY WAY OF REDOX CYCLING, DEVICE THEREFOR AND THE USE THEREOF

The invention relates to a method for producing a device for the electrochemical detection of molecules by way of redox cycling, to a device therefor, and to the use thereof.

BACKGROUND OF THE INVENTION

Redox cycling is an electrochemical process in which electrochemically active molecules are repeatedly oxidized and reduced. These reactions take place between two electrodes located in close proximity to one another. For this purpose, appropriate oxidizing and reducing potentials are applied to the electrodes, whereby the molecules are directly oxidized or reduced upon contact with the electrodes. When the molecule thereafter diffuses to the other electrode, the respective reverse process (reduction/oxidation) takes place. This iterative process causes a charge transport between the electrodes through each individual molecule, which results in amplification of the measurable overall signal.

In the prior art, these types of sensors are produced by way of optical lithography or electron beam lithography. Several designs for redox cycling sensors and methods for the production thereof have been published.

A sensor comprising laterally juxtaposed electrodes is known from Goluch et al. (2009). These so-called "interdigitated electrodes" have a distance in the range of nanometers to micrometers between the individual digits. The method used for production is electron beam lithography, which provides for complex lift-off and etching processes.

Electrodes disposed in the Z axis, which is to say on top of one another, are known from Wolfrum et al. (2008), Kätelhön et al. (2010) and Zevenbergen et al. (2011), and have a nanoscale gap serving as what is known as a "nanocavity" or "nanochannel" therebetween. These are produced by way of electron beam lithography or optical lithography, which comprises multiple etching steps and provides for the removal of a sacrificial chromium layer, among other things.

Hüske et al. (2014) disclose electrodes disposed in the Z axis, which is to say on top of one another, which comprise a nanoscale dielectric between the two electrodes. The electrodes are produced by way of optical lithography and electron beam lithography. The production method includes multiple deposition and etching steps, but also a so-called "self-assembly" step as a result of the anodization of aluminum.

Electrodes disposed in the Z axis, which is to say on top of one another, which include a microscale gap, are known from Gross et al. (2015). The electrodes are produced by adhesively bonding two separate electrodes, comprising a thick layer of dielectric therebetween.

Disadvantages in the Prior Art Include:
 a. Complex manufacturing methods, using photolithography or electron beam lithography, which does not allow economically useful scaling of production.
 b. High costs during production, or non-scalable production processes.
 c. All previous designs require the electrodes and/or an intermediate layer to be post-modified or provided with recognition molecules, such as antibodies, aptamers and the like, so as to detect biomolecules, such as antigens, antibodies, DNA, or the like. These are time-consuming and cost-intensive.
 d. Inadequate sensitivity of microscale redox cycling sensors.
 e. Mechanical instability if gaps are very small.
 f. Etching steps or multiple chemical steps during fabrication.
 g. Some steps of existing methods are difficult to reproduce.

Additional Disadvantages of the Methods Include:
1. Regarding Goluch et al. 2009: The method results in very high production costs due to electron beam lithography being employed. Additionally, delamination of the individual digits occurs with very small lateral distances. If distances are larger, the sensitivity is insufficient due to lower efficiency of the redox cycling process.
2. Regarding Wolfrum et al., Kätelhön et al. 2010, and Zevenbergen et al.: These methods likewise cause high production costs due to the optical or electron beam lithography employed. Moreover, multiple lithography processes having very good alignment are required for the sensors to function. Very small gaps and/or laterally wide gaps result in mechanical instability. In addition, etching steps are necessary for removal of the sacrificial layer, which allow the formation of the intermediate layer after etching.
3. Regarding Hüske et al. 2014: This is a production method that is difficult to reproduce due to the variations in the anodization steps. The method alternatively uses electron beam lithography, which results in very high production costs. Multiple chemical steps and washing steps are needed during fabrication.
4. Regarding Gross et al. 2015: This is a production method that is difficult to reproduce, having very low efficiency in the redox cycling process.

SUMMARY OF THE INVENTION

It is the object of the invention to provide an inexpensive and rapid method for producing a device for the electrochemical detection of molecules by way of redox cycling. The method is to provide mechanically stable devices reproducibly and quickly, at low costs. It is a further object of the invention to provide an associated device for the electrochemical detection of molecules by way of redox cycling and to present options for use thereof.

The object is achieved by the claimed inventions and embodiments thereof.

The method for producing a device for the electrochemical detection of analytes by way of redox cycling is characterized by the following steps:
 a) disposing a first electrically conductive electrode on a substrate;
 b) disposing a dielectric layer pervious for redox-active molecules on the first electrode, including an access for introducing redox-active molecules or analytes into the dielectric layer; and
 c) disposing a second electrically conductive electrode, comprising a conductor track, on the dielectric layer;
 wherein at least one of the steps a) to c) is carried out by way of a method of printing electrically conductive and/or electrically insulating particles.

Advantageously, a method is thus provided, in which at least one of the steps a) to c) is carried out using a printing method. The printing method is advantageously fast and inexpensive, and very easy to reproduce.

The method for producing the redox cycling sensor thus comprises in particular, but not exclusively, selection of conductive and/or insulating printable particles, by way of which the electrode and/or the dielectric layer can be disposed in a structured manner on top of one another. In particular, but not exclusively, ink jet printing, aerosol jet methods, screen printing, intaglio printing, offset printing, nanoimprint methods or hot embossing are employed. It is possible to carry out combinations of coating and ablation steps, which apply identical layers, in combination with different coating methods, such as slot die, laser ablation and so forth.

Printable particles within the meaning of the invention, and preferably nanoparticles, are present in an ink, or in a paste, or in another carrier medium for the particles, for example.

Glass, silicon or a polymer can be selected as the substrate, for example. Various polymers are particularly suitable, such as polyethylene naphthalate, polyethylene terephthalate, polyimide, polymethyl methacrylate, polycarbonate and the like.

According to step a), a first electrode made of conductive particles, such as gold, silver, platinum, carbon, a conductive polymer, such as poly(3,4-ethylenedioxythiophene)polystyrene sulfonate, polyaniline, polypyrrole or the like, and a conductor track are disposed on the substrate, for example by way of ink jet printing methods or another printing method, and converted into a finished structure. The first electrode has either no pores, or only very small pores. The first electrode is to be conductive and preferably have good electrochemical properties, which is to say, for example, have fast electrode kinetics with standard redox mediators, and is to be resistant to electrode contamination by adsorption and/or corrosion to as great an extent as possible.

According to step b), a dielectric layer permeable by redox-active molecules is disposed on the first electrode, including an access for introducing redox-active molecules into the dielectric layer.

Step b) can be carried out in a variety of ways. The access can be created, for example, by disposing a porous dielectric layer on the first electrode in step b), in which the pores extend to the surface of the first electrode. The dielectric layer is preferably printed onto the first electrode.

The size of the nanoparticles for the dielectric layer should be selected to be larger than pores possibly present in the first electrode, so that the nanoparticles for the creation of the dielectric do not penetrate into the pores of the first electrode. The nanoparticles are again present in an ink, a paste or another carrier medium.

Thereafter, in step c), a porous second electrically conductive electrode, preferably comprising a conductor track, can optionally also be disposed on the porous dielectric layer, in which the pores extend to the surface of the dielectric layer. The pores of the second electrode and of the dielectric then form the access for the redox-active material. By applying a redox-active molecule present in solution onto the surface of the second electrode, this finds its way, via the pores of the second electrode and the pores of the dielectric layer, to the surface of the first electrode. The electrodes proper do not have any electrical contact with one another.

The size of the nanoparticles for the second electrode should be selected to be larger than the pores present in the dielectric, so that the nanoparticles for the creation of the second electrode do not penetrate into the pores of the dielectric. The nanoparticles are again present in an ink, a paste or another carrier medium.

In an advantageous embodiment of the invention, the method for producing a device for the electrochemical detection of redox-active molecules by way of redox cycling is thus characterized by the following steps:

a) disposing a first electrically conductive electrode on a substrate;

b) disposing a porous dielectric layer on the first electrode, in which the pores extend to the surface of the first electrode; and c) disposing a porous second electrically conductive electrode on the dielectric layer, in which the pores extend to the surface of the dielectric layer;

wherein at least one of the steps a) to c) is carried out by way of a method of printing electrically conductive and/or electrically insulating particles.

It goes without saying that the electrodes must be designed so as to be contactable.

In this way, a porous dielectric layer is disposed at least on the first electrode, in which the pores extend to the surface of the first electrode. The pores in the dielectric layer are subsequently filled with the molecule or analyte or redox mediator to be reacted.

It is conceivable to dispose the second electrode without a pore system. The access of redox-active molecules to the dielectric layer should then take place by way of lateral access, for example. Such access may, alternatively, also be established by a single opening in the second electrode, such as pinhole-like opening.

According to step b) of the method according to the invention, preferably, an ink comprising dielectric nanoparticles is printed onto the active region of the first electrode. This ink comprises nanoparticles, such as polymethyl methacrylate, polystyrene, silicon oxide, titanium oxide or the like, serving as the functional material.

In the active region, which is to say the region of the reaction of the molecule at the first electrode, the nanoparticle size in the ink for the dielectric layer should be selected so as not to be smaller, and preferably to be larger, than pores possibly present in the first electrode, so that the nanoparticles in the ink of the dielectric do not penetrate into the pores of the first electrode.

In the case of printed ink, this may advantageously be subsequently sintered, such as thermally, photonically, by way of UV or similar energy input, so that the nanoparticles fuse only partially and form a homogeneous dielectric layer comprising uniformly distributed pores having a defined size, which extend to the surface of the first electrode and expose the same.

Alternatively, the dielectric above the first electrode may also not be sintered, so that the nanoparticles remain unchanged, and in this way the porosity with respect to the surface of the first electrode is preserved.

It is particularly advantageously possible to use sol gel inks for producing the dielectric nanoporous layer of the sensor in step b). The material or the ink for the porous dielectric layer is to be prepared such that, after the deposition, for example by way of ink jet printing, this layer dries and/or cures and has the desired porosity, so that contiguous pores are present in the layer. The layer has an access to the liquid, such as via the pores. Such a layer can be produced by using sol gel materials and a sol gel ink. For this purpose, a silicate used for the sol gel may be tetramethyl orthosilicate (TMOS), tetraethyl orthosilicate (TEOS) or tetraisopropyl orthosilicate (TiPOS) for example. However, other materials such as aluminum (2-propylate), aluminum (2-butylate), zirconium propylate, titanium ethylate, titanium (2-propylate) and the like may also be used. Different materials comprising OH groups may be used as the solvent or active material for the condensation reaction of the sol gel. Among other things, water, alcohols (such as ethanol, methanol and the like), various glycols such as ethylene glycol, diethylene glycol, triethylene glycol, propylene glycol, dipropylene glycol, tripropylene glycol and the like, as well as polyglycols having varying chains lengths, for example of 200, 300, 400 or more monomer units, such as polyethylene glycol, polypropylene glycol and glycerol can be used. In addition to the above-mentioned solvents or the mixtures thereof, the ink may also include additives such as surface tension modifiers, tackifiers, adhesion promoters, binding agents and the like.

The sol gel formation of a silica gel on the punctiformly applied dielectric follows the steps as described in the publication "The Sol-Gel Preparation of Silica Gels" (Buckley, A M, Greenblatt, M. 1994. Journal of Chemical Education. Volume 71, No. 7, 599-602), the content of which is hereby incorporated in the present patent application by reference, in particular for the production of the sol gel. In one advantageous embodiment of the invention, this ink also already achieves the object of the invention.

According to step c), a second electrode is disposed on the dielectric. For this purpose, an ink comprising conducting nanoparticles can advantageously be printed onto a nanoporous dielectric layer, and laterally beyond that, so as to form conductor tracks, whereby contact can also be established with this second electrode. The ink advantageously likewise comprises nanoparticles, for example made of gold, platinum, carbon, a conductive polymer, such as poly(3,4-ethylenedioxythiophene)polystyrene sulfonate, polyaniline or the like, serving as the active material. The nanoparticle size in the second electrode is preferably larger than the pores in the dielectric layer beneath. This advantageously prevents the nanoparticles of the second electrode from penetrating into the pores of the dielectric and creating a short circuit with the bottom electrode.

In the present invention, dielectric or dielectric layer shall only refer to the region that serves as a reservoir for the molecule between the electrodes, but not possibly present passivation layers outside the active region. The pore system in the dielectric is the reservoir for the molecule present in solution. The redox reaction of the molecule takes place in the reservoir.

Identical or non-identical materials, such as inks, can be used for disposing the two electrodes, provided that a suitable voltage can be applied to these, which makes the redox reaction of the molecule possible.

The dielectric in the active region of the device is preferably produced from dielectric polymers, such as polyimide, polymethyl methacrylate, other acrylic-based polymers, polyvinyl phenol, ceramic materials and oxides, such as silicon dioxide, titanium dioxide, silicon nitride and the like.

Particularly advantageously, an ink jet printing method is used for the arrangement of at least one of the two electrodes and/or additionally the dielectric layer. Ink jet printing is fast and inexpensive, while offering small dimensions and high reproducibility for the electrodes and dielectric layers to be disposed.

With ink jet printing, for example, ink comprising conductive and/or insulating particles is printed. The particles are optionally sintered, such as thermally, photonically, by way of UV or similar energy input. This advantageously causes a homogeneous conducting and/or insulating layer to be formed. It is also conceivable to use colloidal dissolved gold or carbon, or dissolved polymers, as inks.

In general, when printed ink is used, this is optionally sintered, such as thermally, photonically, by way of UV or by similar energy input. This advantageously causes a homogeneous conducting or insulating layer or a region comprising a plurality of nanopores to be formed. The second top electrode has no ohmic or electrical contact with the bottom first electrode. As a result, the two electrodes are able to form an electrode pair for the redox cycling process.

The active region of the device thus generally provides for the arrangement of at least one electrode and/or of the dielectric by way of a printing method, which yields corresponding sensors for redox cycling quickly and inexpensively.

The active region of the device is the region in which the reaction of the redox-active molecule takes place locally at the two electrodes above and beneath the dielectric layer or the reservoir. The surface area of this part, this being the reservoir, of the dielectric layer is preferably limited to approximately 1 $\mu m^2$ to 1 $cm^2$. The range of the size is preferably between 100 $\mu m^2$ and 1 $mm^2$. The thickness of the dielectric is preferably 10 nm to 1000 nm.

In one advantageous embodiment of the invention, all of the steps a) to c) are carried out using a printing method, and preferably by way of ink jet printing. This advantageously allows a particularly inexpensive, and at the same time fast and reproducible, method for producing the sensor to be provided.

Moreover, particularly advantageously all of the steps a) to c) can be carried out using a printing method, and preferably by way of ink jet printing, in which particles are printed, wherein smaller particles are printed in step a) than in step b) and/or smaller particles are printed in step b) than in step c). An ink jet printing method is advantageous since it offers particularly high throughput, along with high reproducibility and accuracy. The particles present in the printable inks or other starting materials, such as printable pastes, then become increasingly larger in the active region of the device from step a) to step c).

The method can then be carried out in such a way that, in step a) of the method, inks are selected that comprise smaller particles than in step b), and/or in step b) of the method, inks are selected that comprise smaller particles than in step c).

Within the scope of the invention, it is possible to produce pores in the second electrode that are larger than the pores in the dielectric layer and/or to produce pores in the dielectric layer that are larger than pores in the first electrode, provided this even has pores.

In general, the method can be characterized by the selection of an ink comprising conductive particles made of gold, platinum, silver, carbon or conductive polymers, such as poly(3,4-ethylenedioxythiophene)polystyrene sulfonate or polyaniline, for the production of the two electrodes.

The method can advantageously comprise at least one sintering process for printed conductive and/or insulating particles.

In a further embodiment of the invention, a passivation layer for passivating the first electrode can be disposed between the first electrode and the second electrode. This passivation layer likewise advantageously prevents electrical contact from occurring between the electrodes. The passivation layer can preferably comprise a recess for the dielectric.

Further intermediate layers made of dielectric nanoparticles can be disposed on the first electrode in the active region, for example made of polymers, such as polyimide, polymethyl methacrylate, other acrylic-based polymers, polyvinyl phenol, and also made of ceramic materials and oxides, such as silicon dioxide, titanium dioxide, silicon nitride and the like, but also those made of porous hydrogels.

In one advantageous embodiment of the invention, a biofunctionalized ink is selected for disposing the dielectric layer on the first electrode in the active region, or is disposed thereon. This advantageously allows the sensor to be used for the indirect detection of the biological or biochemical molecules.

Selecting an ink comprising insulating particles for producing the dielectric layer, to which, prior to printing, antibodies, receptors, DNA, enzymes or other biomolecules have already been bound, advantageously allows the complementary biomolecules, such as antigens, to be indirectly detected, or electrochemically active products of the enzymatic activity to be directly detected. In the case of a bound antibody, the indirect detection takes place by way of a redox mediator. The complementary antigens partially block the pores and thereby reduce the redox cycling current of the redox mediator. Reducing the redox cycling current quantitatively corresponds to the blocked surface area, which is to say the concentration of the antigen. In the case of a bound enzyme, a substrate is processed, whereby redox-active products are generated. These redox-active products can be reduced and oxidized between the two electrodes of the redox cycling sensor, and thereby amplify the signal. In this case, the redox cycling current corresponds to the concentration of the enzyme substrate.

The advantage of this last method can be seen in that the biofunctionality is already achieved prior to printing as a result of the selection of an appropriate ink, whereby time-consuming and cost-intensive post-treatments are avoided.

The device according to the invention for the electrochemical detection of molecules by way of redox cycling thus comprises a first electrically conductive electrode on a substrate. A dielectric layer permeable by redox-active molecules is disposed on the first electrode, including an access for introducing redox-active molecules into the dielectric layer. A second electrically conductive electrode, having no electrical contact with the first electrode, is disposed on this dielectric layer.

The redox reaction of a molecule, such as of an analyte, takes place at the electrodes, wherein the dielectric layer forms the reservoir for the molecule present in solution.

According to the invention, at least one of the two electrodes is composed of printed electrically conductive particles and/or the dielectric layer is composed of printed electrically insulating particles.

A porous dielectric layer is disposed on the first electrode, in which pores in the dielectric layer extend to the surface of the first electrode. The access of the redox-active substance into the reaction region can then take place directly via the surface of the second electrode, as well as the pore system of the second electrode and the pore system of the dielectric.

In one advantageous further embodiment of the invention, a porous second electrically conductive electrode, having no electrical contact with the first electrode, is disposed on the dielectric layer.

In the device, the two electrodes of the device are working electrodes in a potentiostat, which are present in contact with a reference electrode and/or a counter electrode.

The device according to the invention for the electrochemical detection of molecules by way of redox cycling then preferably comprises a first electrically conductive electrode on a substrate. A porous dielectric layer is disposed on the first electrode, in which the pores in the dielectric layer extend to the surface of the first electrode. A porous second electrically conductive electrode, having no electrical contact with the first electrode, is disposed on this dielectric layer. The redox reaction of the molecule, or of an analyte, or of a redox mediator, takes place at the two electrodes. The dielectric layer is a reservoir for the molecule present in solution. At least one of the two electrodes is composed of printed electrically conductive particles and/or the dielectric layer is composed of printed electrically insulating particles. This region of the device marks what is known as the active region of the device, which is used to react the molecule, or analyte, or redox mediator.

In the device, the conductive particles of the second electrode are advantageously larger than the pores in the dielectric layer therebeneath and/or the insulating particles of the dielectric layer are larger than the pores in the first electrode therebeneath. This likewise causes the electrochemical properties of the electrodes and of the dielectric to be preserved.

The two electrodes of the device represent the working electrodes in a potentiostat and make contact with a reference electrode and/or a counter electrode. The reference electrode defines the potentials applied to the working electrodes, which are above and below the redox potential of the molecule or analyte and/or of the redox mediator, so that this is alternately reduced and oxidized at the two electrodes. The resulting flow of current is indicated by measurement of the current by way of a counter electrode.

The dielectric layer particularly advantageously has a surface area between at least 1 $\mu m^2$ and no more than 1 $cm^2$ in the active region of the sensor. This advantageously results in the generation of radial mass transport to the electrodes and rapidly achievable steady state signals.

The range of the size is preferably between 100 $\mu m^2$ and 1 $mm^2$. The thickness of the dielectric is preferably 10 nm to 1000 nm.

The active region of the sensor or active material thus denotes the region of the electrodes and of the dielectric at which the redox cycling of the molecule is carried out. The active material of the dielectric is thus the region of the dielectric that is disposed directly between the active region of the electrodes, and serves as the reservoir for the molecule present in solution, or the analyte/redox mediator present in solution.

The object of the invention is also achieved by the sensitive detection of redox-active molecules by way of the at least partially printed redox cycling sensor.

It was found, within the scope of the invention, that a special arrangement of the electrodes is necessary for implementing such a sensor, in which the electrodes are located very close to one another. The efficiency of redox cycling or of the amplification of the signal per molecule is dependent on the square of the distance between the electrodes. This is why a nanoscale distance between the first and second electrodes is desirable in the devices according to the invention for redox cycling, which allows the most sensitive detection.

It goes without saying that the sensor can be used as a redox-active molecule and for the detection of the redox reaction by introducing a solution comprising a molecule or analyte or redox mediator. This is present in solution and is applied to the pores of the second electrode above the porous dielectric layer in the reservoir. Alternatively, it will reach the dielectric, for example through a lateral or other vertical access. The molecule diffuses back and forth between the pores of the dielectric layer. The voltages applied to the first electrode and to the second electrode drive the reduction and oxidation of the molecule or analyte (redox mediator) at the two electrodes above and beneath the reservoir, and generates a detectable flow of current.

If the redox-active material reaches the dielectric via another access, such as a lateral or vertical access, no pore system of the second electrode is necessary.

The invention is not yet limited to these. It was found, within the scope of the invention that, conventional ink can be used in a printing method for producing a device for the electrochemical detection of analytes by way of redox cycling. This is preferably biofunctionalized.

Thus, in step b), a biomodified, dielectric ink that is disposed on the active region of the first electrode in accordance with step a) may advantageously be present. In general, this ink in step b) comprises nanoparticles, for example polymethyl methacrylate, polystyrene, silicon oxide, titanium oxide and the like, which are equipped with antibodies, DNA, aptamers or the like, where necessary, serving as the active material. The nanoparticle size should not be smaller than the possibly present pores in the first electrode, so that the nanoparticles do not penetrate into the electrode layer. Biofunctionalized ink may only be sintered (thermally, photonically, by way of UV or by other methods) to such an extent that the biochemical units, such as antibodies, DNA, aptamers and the like, do not lose the biological recognition properties thereof, and in particular are not denatured. When using this optional step, a sintering method must be used which does not damage the biological material. In particular, care must be taken to ensure a low temperature in keeping with the biological properties of the layer.

For this purpose, dielectric nanoparticles in an ink are preferably biofunctionalized with the following elements:
   complete antibodies (such as: total IgG, lgG1, lgG2, lgG3, lgG4, IgM, IgD, IgA, lgA1, lgA2, IgE) either recombinant or human, mouse, rat, goat, rabbit or pig antibodies;
   antibodies bound to Protein A, Protein G and Protein L, serving as a biorecognition element;
   fragment antibodies (Fab' fragment), F(ab') which were generated enzymatically (for example, cysteine, papain, pepsin, ficin, bromelain) or by way of photonic activation;
   single-chain fragment variable (scFv);
   artificial baroreceptors, such as aptamers and molecularly imprinted polymers (MIPs);
   enzymes that are electrochemically active (such as glucose oxidase) and convert a substrate into a redox-active material, which can then be amplified using redox cycling;
   the material of the substrate is preferably selected from glass, silicon, various polymers, such as polyethylene naphthalate, polyethylene terephthalate, polyimide, polymethyl methacrylate, polycarbonate and the like;
   the electrodes are preferably produced from gold, platinum, silver, carbon in various forms (carbon nanoparticles, graphite, graphene, carbon nanotubes, diamond, and the like), conductive polymers, such as poly (3,4-ethylenedioxythiophene) polystyrene sulfonate, polyaniline, and the like.

It is thus also possible to indirectly detect even molecules and analytes that are not redox-active, by way of redox cycling. This detection can take place by immobilizing antibodies, DNA, aptamers and the like on one of the two or on both electrodes and/or on the dielectric or the dielectric layer. When adding an analyte that comprises not only redox-active molecules, but also the complementary antigens, DNA and the like, these will specifically bind to the immobilized antibody, DNA, aptamer and the like. The surface area available for the electrochemical reactions is consequently decreased. As an alternative, the diffusion pathway of the redox-active material is extended by the blockage caused by the specific bonds. This results in a change in the redox cycling current, which can be measured by way of a potentiostat. Since the blocked surface and the concentration of the complementary antigens, DNA and the like are related in terms of scaling, such a sensor can be used as a quantitative immunosensor.

When immunosensors are used as a point-of-care diagnostic tool, the price thereof is an important criterion. In most instances, the price for disposable sensors should be less than € 1 per piece. This price is not achievable with today's production methods for redox cycling sensors. Additionally, today's production methods always necessitate a post-modification step for the immobilization of the antibodies, which further drives up the per-piece cost.

The method presented here, in contrast, achieves the object by selecting an ink comprising biomodified nanoparticles from the start for the arrangement of the dielectric layer, the ink subsequently, which is to say also after sintering, having the biological function thereof.

Ultimately, a device for the electrochemical detection of molecules by way of redox cycling is again provided, in which a first electrically conductive electrode is disposed on a substrate, a biofunctionalized, porous dielectric layer is disposed on the first electrode, in which the pores extend to the surface of the first electrode, and a preferably porous second electrically conductive electrode is disposed on the dielectric layer, wherein the nanoparticles of the second electrode, or of the ink for the second electrode, are larger than the pores in the dielectric. As an alternative, the second electrode is pore-free, and the access of the redox-active material takes place via a different access to the dielectric, such as laterally.

In general, the term 'pores' is defined as follows in the present patent application. Pores in the dielectric layer and/or in the electrodes are preferably not pinhole-like or stitching needle-like.

The pores preferably have a sponge-like nature, as a result of the printing method, and in particular as a result of an ink jet printing method, and as a result of sintering optionally taking place thereafter. The production method according to the invention thus causes sponge-like pore systems in the dielectric, or in the electrode or electrodes.

The pores are to be distributed as evenly as possible in the electrode(s) and/or the dielectric. The pores in one of these layers can either be ordered, such as by a plurality of channel-shaped, continuous pores (plurality greater than two pores), or by a hexagonal arrangement of the nanoparticles and formation of the pores. The pores, however, may also be disordered (such as sponge-like porosity). The particles from the top layer should preferably always be larger than the pores of the layer underneath.

The pore size of the first electrode is preferably 0 to 50 nm in diameter.

The pore size of the dielectric is preferably 10 to 1000 nm in diameter.

The pore size of the second electrode is preferably 100 to 10000 nm in diameter. Alternatively to a pore system, it is also possible to provide only a single large, such as annular, opening, in the second electrode as the access for the redox-active material.

Specifically, a porous dielectric can be composed of a sponge-like skeleton made of optionally partially fused and non-conductive particles, which is permeated by pores extending from the surface of the dielectric to the opposite surface to the first electrode.

Optionally, specifically, a porous electrode, and in particular a porous second electrode on the dielectric, may be composed of a sponge-like skeleton made of optionally fused and conductive particles, which is permeated by pores extending from the surface of the second electrode to the opposite surface of the dielectric. Access by the molecule is then possible by applying a solution comprising molecules to the surface of the second electrode and the pore system of the second electrode and the dielectric, up to the first electrode. A redox-active molecule that is applied to the surface of the second electrode of such a sensor thus reaches the surface of the first electrode via the pore system of the second electrode and the pore system of the dielectric, and can be alternately reacted. This can be reduced and oxidized in a manner corresponding to the voltages applied to the surfaces of the two electrodes.

If another access for the molecule leads into the dielectric, such as a lateral access, for example via the passivation layer, no pores are necessary in the second electrode in the active region.

The use of the at least partially printed redox cycling sensors falls within the field of direct detection of chemical analytes, in particular for the detection of antigens.

Brief Description of the Drawings

The invention will be described in more detail hereafter based on exemplary embodiments and the accompanying figures, without thereby limiting the invention.

IN THE DRAWINGS

DESCRIPTION OF THE PREFERRED EMBODIMENTS

First Exemplary Embodiment

A sensor comprising sponge-like pores in the second electrode and in the dielectric is produced by way of the above-described method.

Step a): A gold ink is selected as the material for the first electrode 2a. The conducting structures made of the gold ink are printed onto a polyethylene naphthalate (PEN) substrate 1 using an ink jet printer, and are then sintered at 125° C. for 1 hour.

In this way, a first electrode 2a is formed on the substrate 1, which has either no pores or pores having a maximum size of 20 nm.

Figure 1:
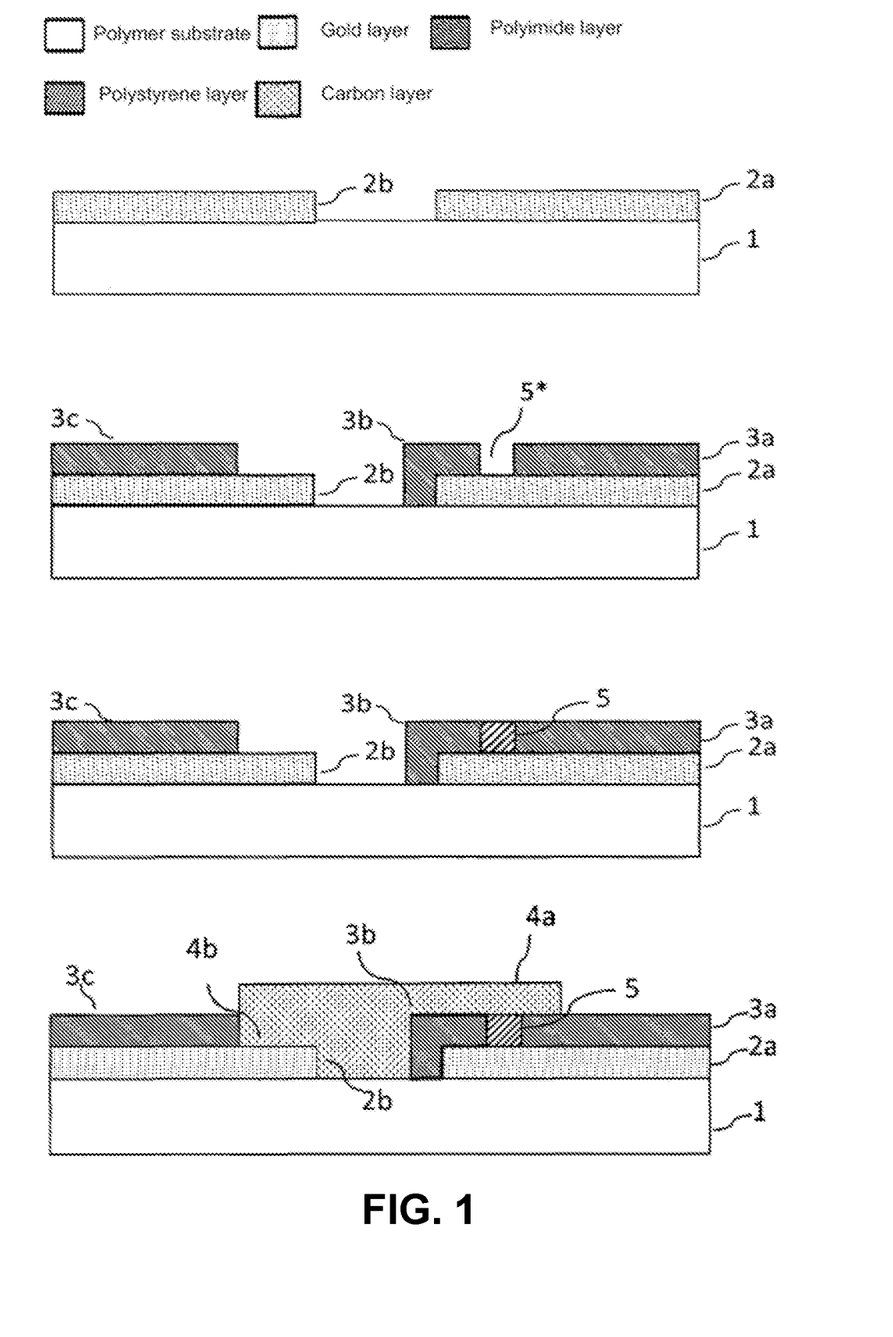
FIG. 1 shows a method according to the invention.

FIG. 1 shows a right region of the electrode 2a, which defines the active measuring region for the reaction of the redox-active substance (not shown). Furthermore, a left region made of sintered gold ink 2b on the substrate 1 is shown, to which a voltage is applied and which thus represents a conductor track. The region 2a of the first electrode extends to the right out of the image plane and is contacted with a potentiostat to apply voltage.

Passivation: An ink made of polyimide is selected. Using this ink, recesses 5*measuring approximately 100×100 μm2 are defined as electrode regions by way of ink jet printing, as shown in the right part of FIG. 1 (active region). The polyimide ink is disposed thereon so as to passivate the first electrode 2a. In this way, the right active region of the first electrode 2a is passivated around the region 5*. The passivation ink is printed as passivation layers 3a, 3b around the later dielectric 5, so that a region 5*is recessed for the later dielectric 5.

In addition, a portion of the conductor track 2b made of gold is passivated by way of polyimide. In the left inactive region of FIG. 1, the polyimide layer 3c is thus disposed on the conductor track 2b in such a way that the conductor track is partially exposed on the side facing the first electrode 2a, and a step-like arrangement of polyimide 3c and conductor track 2b is produced on the substrate 1.

The passivation layers 3a, 3b and 3c are disposed in a single method step. It goes without saying that the regions of the first electrode 2a and of the conductor track 2b lying in the depth of the image are completely passivated.

Step b) Non-biomodified polystyrene nanoparticle ink comprising nanoparticles 100 nm in size is disposed in the recessed region 5*of the passivation 3a, 3b in the active region of the sensor by way of ink jet printing. This dielectric 5 or this layer 5, due to the porosity thereof, forms a reservoir for the molecule present in solution and to be reacted, or for the analyte/redox mediator. This layer has dimensions of approximately 100 μm×100 μm at a height of 500 nm.

The dielectric 5 is sintered at 115° C. for 5 minutes, so that a homogeneous nanoporous layer 5 is formed as a result of the partial fusion of the particles.

The pore size in the dielectric is approximately 30 nm in diameter.

Step c): Carbon ink comprising carbon nanoparticles of 300 to 400 nm in size is selected as the second, top electrode 4a and disposed on the passivation 3a, 3b and the dielectric 5. The ink is also partially printed onto the passivation layer 3a, 3b and onto the dielectric 5 in the region of the first electrode 2a, and moreover in the inactive region of the sensor, which is shown on the left in FIG. 1, so as to form further contact points for the second electrode in the region 4b via the conductor track 2b. The ink is sintered at 125° C. for 1 hour.

The pore size in the second electrode is approximately 100 nm in diameter.

In addition to the active region for the redox reaction in the right part of FIG. 1, a further particularly advantageous embodiment of the method and of a device thus produced is shown in the left part of FIG. 1. This left region is the so-called inactive region of the sensor. The inactive region comprises the conductor track 2b made of gold, which extends out of the image plane to the left (not shown). The conductor track 2b is contacted with a potentiostat (not shown).

In this way, a voltage, such as above the oxidation potential of the molecule or analyte/redox mediator, can be applied via the conductor track 2b to the active region of the second electrode 4a, which results in oxidation of the molecule/analyte at the electrode. Correspondingly, a voltage is applied to the active region of the first electrode 2a, which is below the reduction potential of the analyte and thus enables the alternating redox cycling process. The detection, however, can also just as well be carried out conversely, so that the reduction potential is applied to the electrode 4a, and the oxidation potential is applied to the electrode 2a.

A molecule or an analyte, such as ferrocenedimethanol, is applied to the electrode in the form of a solution (oxidized or reduced). The bottom, first electrode in the region 2a and the top, second electrode 4a are accordingly brought in contact and set to an oxidizing potential of +600 mV and a reducing potential of 0 mV with respect to an Ag/AgCl reference electrode. The detection of the analyte in various concentrations takes place by measuring the redox cycling current intensity at the oxidizing and/or reducing electrode.

SECOND EXEMPLARY EMBODIMENT: USE OF THE PRINTED REDOX CYCLING SENSOR FOR THE DETECTION OF OVALBUMIN

A second sensor comprising sponge-like pores in the dielectric and the second electrode is produced as follows by way of an above-described method (FIG. 1):

Steps a) and c) and the passivation follow exemplary embodiment 1.

Step a): A gold ink is selected as the material for the first electrode 2a. The conducting structures made of the gold ink are printed onto a polyethylene naphthalate (PEN) substrate 1 using an ink jet printer, and are then sintered at 125° C. for one hour.

In this way, a first electrode 2a is formed on the substrate 1, which has either no pores or pores having a maximum size of 20 nm.

FIG. 1 shows a right region of the electrode 2a, which defines the active measuring region for the reaction of the redox-active substance (not shown). Furthermore, a left region made of sintered gold ink 2b on substrate 1 is shown, which is used for the application of the voltage and thus represents a conductor track. The region 2a of the first electrode extends to the right out of the image plane and is contacted with a potentiostat to apply voltage.

Passivation: An ink made of polyimide is selected. Using this ink, electrode regions approximately 100×100 μm in size are defined as the recess 5* by way of ink jet printing, as shown in the right part of FIG. 1 (active region). The polyimide ink is provided so as to passivate the first electrode 2a. In this way, the right active region of the first electrode 2a is passivated around the region 5*, this being the subsequent reservoir. The passivation ink is printed as passivation layers 3a, 3b around the later dielectric 5, so that a region 5* is recessed for this dielectric 5.

In addition, a portion of the conductor track 2b made of gold is passivated by way of polyimide. In the left inactive region of FIG. 1, the polyimide layer 3c is thus disposed on the conductor track 2b in such a way that the conductor track is partially exposed on the side facing the first electrode 2a, and a step-like arrangement of polyimide 3c and conductor track 2b is produced on the substrate 1.

The passivation layers 3a, 3b and 3c are disposed in a single method step. It goes without saying that the regions of the first electrode 2a and of the conductor track 2b lying in the depth of the image are completely passivated.

Using this ink, as in exemplary embodiment 1, approximately 100 μm×100 μm electrodes, conductor tracks and contact points for the sensor are again defined.

Step b): 100 nm polystyrene nanoparticle ink, which is to say a polystyrene nanoparticle ink comprising nanoparticles of 100 nm in size, is used. The polystyrene nanoparticles are equipped with anti-ovalbumin antibodies and used as a dielectric 5 or intermediate layer between the two electrodes 2a and 4a. The ink is printed in the region 5*, which was recessed by the passivation layers 3a, 3b so as to define the active region of the electrodes 2a, 4a. The dielectric 5 is heated at 40° C. for 30 minutes, so that the solvents evaporate, but the biological material is not damaged and preserves the function thereof.

The pore size corresponds approximately to that of the first exemplary embodiment.

Step c): Carbon ink comprising carbon nanoparticles of 300 to 400 nm in size is disposed as the top electrode 4a on the passivation layer 3a, 3b and the dielectric 5. The ink is printed onto the passivation layer in the region of the first electrode 2a, and also beyond, so as to form the contact points in the region 4b via the conductor track 2b, and is then sintered, so that the biological material of the dielectric 5 is not damaged.

The pore size corresponds approximately to that of the first exemplary embodiment.

The inactive region thus otherwise corresponds to the inactive region of the first exemplary embodiment, and the contacting of the first electrode 2a and of the generated conductor track 2b beneath the contact region 4b is also identical.

In addition to the active region for the redox reaction in the right part of FIG. 1, a further particularly advantageous embodiment of the method and of a device thus produced is thus shown in the left part of FIG. 1. This left region is the so-called inactive region of the sensor. The inactive region comprises the conductor track 2b made of gold, which extends out of the image plane to the left (not shown). The conductor track 2b is contacted with a potentiostat (not shown).

In this way, a voltage, such as above the oxidation potential of the molecule or analyte/redox mediator, can be applied via the conductor track 2b to the active region of the second electrode 4a above the dielectric 5, which results in oxidation of the molecule/of the analyte at the electrode. Correspondingly, a voltage is applied to the active region of the first electrode 2a which is below the reduction potential of the analyte and thus enables the redox cycling process. The detection can also be carried out conversely, so that the reduction potential is applied to the electrode 4a, and the oxidation potential is applied to the electrode 2a.

A solution comprising ovalbumin and a redox mediator, such as ferrocenedimethanol, is applied to the surface of the second electrode 4a. The bottom electrode 2a and the top electrode 4a are accordingly brought in contact and set to an oxidizing potential of +600 mV and a reducing potential of 0 mV against an Ag/AgCl reference electrode. The detection of the analyte in different concentrations will take place by measuring the redox cycling current intensity.

At higher concentrations of ovalbumin, the redox cycling current intensity will decrease, since the available electrochemical surface also decreases with the concentration.

Figure 2:
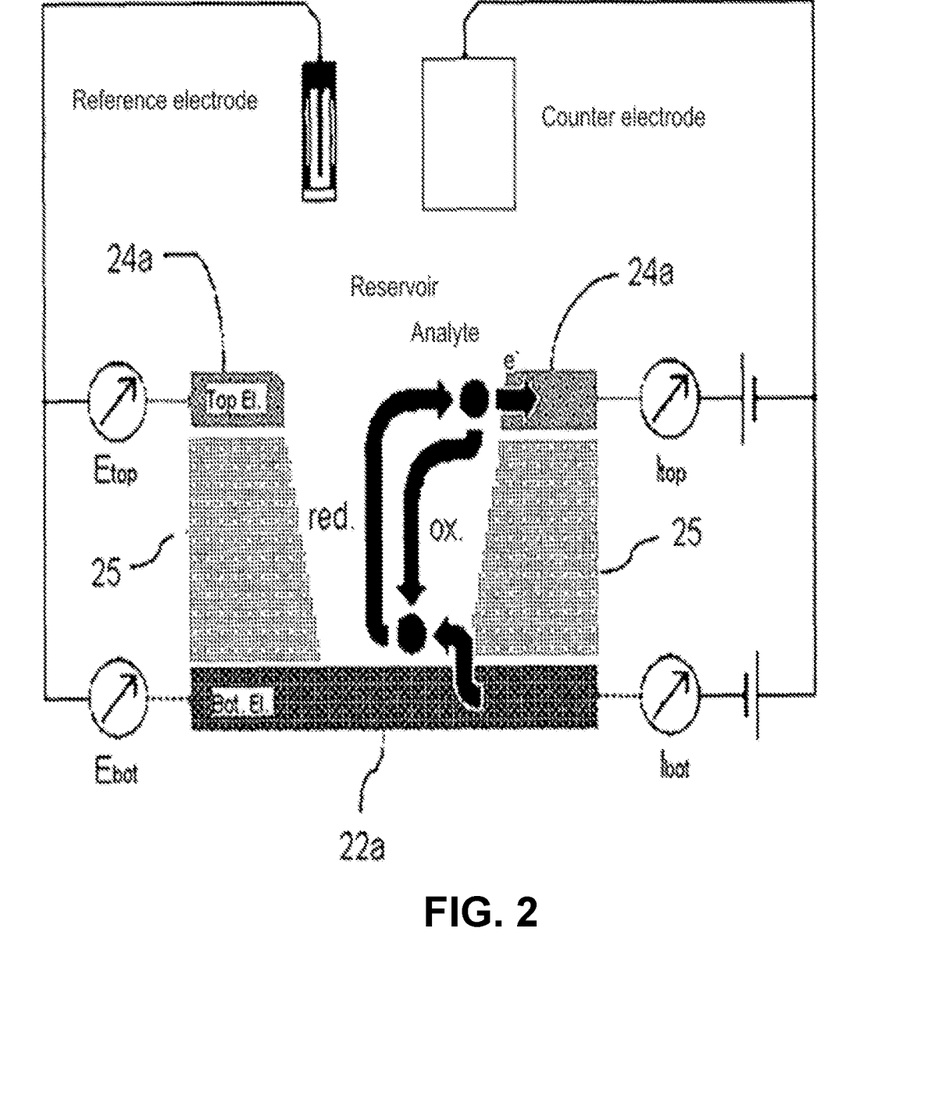
FIG. 2 shows a device according to the invention.

FIG. 2 shows a schematically illustrated device, which is simplified compared to FIG. 1, in the active region, the cyclical reaction of an analyte at a first electrode 22a or Bot. El. and a second electrode 24a or Top. El. and the arrangement thereof in the potentiostat.

The porous dielectric 25, which serves as the reservoir for the analyte/redox mediator present in solution, is disposed between the two electrodes. Voltages are applied to the porous second electrode 4a and the first electrode 2a, which drive the cyclical redox reaction. The generated current is correspondingly measured against the counter electrode.

According to the invention, a nanoscale redox cycling sensor is thus produced only by way of printing technologies, without additional etching steps or sacrificial layers, and optionally also by way of biomodification without further steps.

The object is achieved by a design comprising electrodes disposed in the Z axis on top of one another, which comprise a nanoscale dielectric between the electrodes, wherein the electrodes and/or the dielectric are completely printed. Advantageously, there are no etching steps in the method. This is achieved in that the three layers (1. first bottom conducting electrode; 2. dielectric layer; 3. second top conducting electrode) have differing porosities. Every further layer has larger particles than the layer disposed beneath, so that the layer 4a lying on top, upon deposition from the liquid phase (such as ink jet printing), cannot flow into the layer 5 lying at the bottom, and cannot flow from layer 5 into layer 2a.

For the exemplary embodiments, an OJ300 ink jet printer from UniJet (Korea) was used.

The Teonex (PEN) substrate was obtained from DuPont-Teijin Films (England).

The Au25 gold ink was obtained from UT Dots (USA).

Polymer inks such as polyimide (PI) PMA-1210P-004 was obtained from Sojitz (Japan). Polystyrene nanoparticle ink was mixed from 200 nm polystyrene beads from Polysciences (USA).

Carbon ink 3800 was obtained from Methode (USA).

Further Exemplary Embodiments:

These relate to the use of the sol gel inks for creating the nanoporous dielectric. In the first exemplary embodiment in step b), for example, the nanoporous dielectric can be provided as follows.

In step b), a non-biomodified sol gel-based ink is prepared. For this purpose, TMOS 1:1:1 (percent by weight) is mixed with deionized water and glycerol in a 100 ml flask and stirred for one hour at room temperature using a magnetic stirrer on a magnetic plate. Afterwards, a 100 mM solution of hydrochloric acid at 500:1 (sol gel:acid, percent by weight) is added for starting the condensation reaction. The sol gel ink is disposed in the recessed region 5* of the passivation 3a, 3b in the active region of the sensor by way of ink jet printing. The dielectric 5 or the layer 5, 25, due to the porosity thereof, forms the reservoir for the molecule present in solution and to be reacted, or for the analyte/redox mediator, after hydrolysis and curing. This layer has dimensions of approximately 100 µm×100 µm at a height of approximately 500 nm.

The dielectric 5, 25 is sintered at room temperature for 60 minutes, so that a homogeneous nanoporous layer 5 forms as a result of the condensation reaction in the printed sol gel layer. The pore size in the dielectric is then approximately 20 to 40 nm in diameter.

It goes without saying that a person skilled in the art can also use other sol gel materials that are subject to an acid-catalyzed and/or base-catalyzed condensation reaction and hydrolysis.

LIST OF REFERENCES

Goluch E. D., Wolfrum B., Singh P. S., Zevenbergen M. A. G., Lemay S. G. (2009). Redox cycling in nanofluidic channels using interdigitated electrodes. Anal Bioanal Chem 394:447-456

Wolfrum B., Zevenbergen M., Lemay S. (2008). Nanofluidic redox cycling amplification for the selective detection of catechol. Anal Chem 80, 972-977

Kätelhön E., Hofmann B., Lemay S. G., Zevenbergen M. A. G., Offenhäusser A., Wolfrum B. (2010). Nanocavity Redox Cycling Sensors for the Detection of Dopamine Fluctuations in Microfluidic Gradients. Anal Chem 82, 8502-8509

Zevenbergen M. A. G., Singh P. S., Goluch E. D., Wolfrum B. L., Lemay S. G. (2011). Stochastic sensing of single molecules in a nanofluidic electrochemical device. Nano Lett. 11, 2881-2886

Hüske M., Stockmann R., Offenhäusser A., Wolfrum B. (2014). Redox Cycling in nanoporous electrochemical devices. Nanoscale 6, 589-598

Gross A. J., Holmes S., Dale S. E. C., Smallwood M. J., Green S. J., Winlove C. P., Benjamin N., Winyard P. G., Marken F. (2015). Nitrite/Nitrate detection in serum based on dual-plate generator-collector currents in a microtrench. Talanta 131:228-235

The invention claimed is:

1. A device for electrochemical detection of redox-active molecules by way of redox cycling, comprising:
   a first electrically conductive electrode disposed on a substrate,
   a passivation layer covering the first electrically conductive electrode at a surface opposite the substrate, the passivation layer having a through-opening;
   a dielectric layer permeable by said redox-active molecules disposed in the through opening on the first electrically conductive electrode, and
   a second electrically conductive electrode, having no electrical contact with the first electrode, disposed on the passivation layer and covering the dielectric layer, the second electrically conductive electrode having an access for or being permeable to said redox-active molecules,
   wherein redox cycling of redox-active molecules permeating the dielectric layer takes place at least at portions of the first electrically conductive electrode and second electrically conductive electrode that are in contact with the dielectric layer,
   wherein the dielectric layer is a reservoir for the redox-active molecules present in a solution, a pathway for the redox-active molecules to enter the reservoir being comprised by the second electrically conductive electrode through which said redox-active molecules migrate from an exposed surface of the second electrically conductive electrode through the second electrically conductive electrode into the dielectric layer,
   wherein at least one of the first electrically conductive electrode and second electrically conductive electrode comprises printed electrically conductive particles, and wherein the passivation layer comprises printed electrically insulating particles, and
   wherein the first electrically conductive electrode and the second electrically conductive electrode of the device are working electrodes in a potentiostat, which are in contact with either one or both of a reference electrode and a counter electrode.

2. A device according to claim 1, wherein the dielectric layer has a surface area between at least 1 µm$^2$ and no more than 1 cm$^2$.

3. The device according to claim 1 operated by a method comprising:
   introducing said solution comprising redox-active molecules into the dielectric layer, and
   applying a voltage to the electrodes so causing alternating reduction and oxidation of the redox-active molecules at the first and second electrically conductive electrodes.

4. The device according to claim 3, wherein said introducing comprises migrating redox-active molecules in solution through pores of the second electrically conductive layer into the dielectric layer.

5. The device according to claim 4, wherein the first electrode has a pore size that is 0 to 50 nm in diameter, the dielectric layer has a pore size that is 10 to 1000 nm in diameter, and the second electrode has a pore size that is 100 to 10000 nm in diameter.

6. The device according to claim 1,
wherein the first electrode comprises conductive particles made of gold, platinum, silver, carbon poly(3,4-ethylenedioxythiophene)polystyrene sulfonate or polyaniline; and
wherein the second electrode comprises conductive particles made of gold, platinum, silver, carbon, poly(3,4-ethylenedioxythiophene)polystyrene sulfonate or polyaniline.

7. The device according to claim 1, wherein the dielectric layer comprises insulating particles, to which enzymes, antibodies, receptors or other biomolecules can bind.

8. A method for electrochemically detecting redox-active molecules by way of redox cycling comprising:
providing a device comprising:
a first electrically conductive electrode disposed on a substrate;
a passivation layer covering the first electrically conductive electrode at a surface opposite the substrate, the passivation layer having a through-opening;
a dielectric layer permeable by said redox-active molecules disposed in the through opening on the first electrically conductive electrode; and
a second electrically conductive electrode, having no electrical contact with the first electrode, disposed on the passivation layer and covering the dielectric layer, the second electrically conductive electrode having an access for or being permeable to said redox-active molecules;
wherein redox cycling of redox-active molecules permeating the dielectric layer takes place at least at portions of the first electrically conductive electrode and second electrically conductive electrode that are in contact with the dielectric layer;
wherein the dielectric layer is a reservoir for the redox-active molecules present in a solution, a pathway for the redox-active molecules to enter the reservoir being comprised by the second electrically conductive electrode through which said redox-active molecules migrate from an exposed surface of the second electrically conductive electrode through the second electrically conductive electrode into the dielectric layer;
wherein at least one of the first electrically conductive electrode and second electrically conductive electrode comprises printed electrically conductive particles;
wherein the passivation layer comprises printed electrically insulating particles; and
wherein the method comprises:
introducing said solution comprising redox-active molecules into the dielectric layer, and
applying a voltage to the electrodes so causing alternating reduction and oxidation of the redox-active molecules at the first and second electrically conductive electrodes.

9. The method according to claim 8, wherein said introducing comprises migrating redox-active molecules in solution through pores of the second electrically conductive layer into the dielectric layer.

10. The method according to claim 9, wherein the first electrode has a pore size that is 0 to 50 nm in diameter, the dielectric layer has a pore size that is 10 to 1000 nm in diameter, and the second electrode has a pore size that is 100 to 10000 nm in diameter.

11. The device method according to claim 8,
wherein the first electrode comprises conductive particles made of gold, platinum, silver, carbon, poly(3,4-ethylenedioxythiophene)polystyrene sulfonate or polyaniline; and
wherein the second electrode comprises conductive particles made of gold, platinum, silver, carbon poly(3,4-ethylenedioxythiophene)polystyrene sulfonate or polyaniline.

12. The method according to claim 8, wherein the dielectric layer comprises insulating particles, to which enzymes, antibodies, receptors or other biomolecules can bind.

13. A device for electrochemical detection of redox-active molecules by way of redox cycling, comprising:
a first electrically conductive electrode disposed on a substrate;
a passivation layer covering the first electrically conductive electrode at a surface opposite the substrate, the passivation layer having a through-opening;
a dielectric layer permeable by said redox-active molecules disposed in the through opening on the first electrically conductive electrode; and
a second electrically conductive electrode, having no electrical contact with the first electrode, disposed on the passivation layer and covering the dielectric layer, the second electrically conductive electrode having an access for or being permeable to said redox-active molecules;
wherein redox cycling of redox-active molecules permeating the dielectric layer takes place at least at portions of the first electrically conductive electrode and second electrically conductive electrode that are in contact with the dielectric layer;
wherein the dielectric layer is a reservoir for the redox-active molecules present in a solution, a pathway for the redox-active molecules to enter the reservoir being comprised by the second electrically conductive electrode through which said redox-active molecules migrate from an exposed surface of the second electrically conductive electrode through the second electrically conductive electrode into the dielectric layer;
wherein at least one of the first electrically conductive electrode and second electrically conductive electrode comprises printed electrically conductive particles, and wherein the passivation layer comprises printed electrically insulating particles;
wherein the second electrically conductive layer is formed with a printable ink comprising electrically conductive particles of a size which are larger than pores in the dielectric layer; and
wherein either the first electrically conductive electrode has no pores, or the first electrically conductive electrode has pores that are smaller than a size of dielectric particles in a printable ink used to form the dielectric layer.

14. The device according to claim 13 operated by a method comprising:
introducing said solution comprising redox-active molecules into the dielectric layer, and applying a voltage to the electrodes so causing alternating reduction and oxidation of the redox-active molecules at the first and second electrically conductive electrodes.

15. The device according to claim 14, wherein said introducing comprises migrating redox-active molecules in solution through pores of the second electrically conductive layer into the dielectric layer.

16. The device according to claim 15, wherein the first electrode has a pore size that is 0 to 50 nm in diameter, the dielectric layer has a pore size that is 10 to 1000 nm in diameter, and the second electrode has a pore size that is 100 to 10000 nm in diameter.

17. The device according to claim 13,
wherein the first electrode comprises conductive particles made of gold, platinum, silver, carbon poly(3,4-ethylenedioxythiophene)polystyrene sulfonate or polyaniline; and
wherein the second electrode comprises conductive particles made of gold, platinum, silver, carbon, poly(3,4-ethylenedioxythiophene)polystyrene sulfonate or polyaniline.

18. The device according to claim 13, wherein the dielectric layer comprises insulating particles, to which enzymes, antibodies, receptors or other biomolecules can bind.

* * * * *